United States Patent [19]

Bueschken et al.

[11] Patent Number: 5,728,891
[45] Date of Patent: *Mar. 17, 1998

[54] PROCESS FOR THE PREPARATION OF 3,3, 5-TRIMETHYLCYCLOHEXANONE

[75] Inventors: Wilfried Bueschken, Haltern; Juergen Hummel, Marl, both of Germany

[73] Assignee: Huels Aktiengesellschaft, Marl, Germany

[*] Notice: The term of this patent shall not extend beyond the expiration date of Pat. No. 5,675,045.

[21] Appl. No.: 668,356

[22] Filed: Jun. 26, 1996

[30] Foreign Application Priority Data

Jul. 8, 1990 [DE] Germany .................. 195 24 969.0

[51] Int. Cl.$^6$ .................................................. C07C 49/303
[52] U.S. Cl. .................... 568/376; 568/377; 568/881
[58] Field of Search .............................. 568/376, 377, 568/881

[56] References Cited

U.S. PATENT DOCUMENTS

| | | |
|---|---|---|
| T892,018 | 11/1971 | Wellman et al. . |
| 3,361,822 | 1/1968 | Schmidt et al. ............ 260/586 |
| 3,446,850 | 5/1969 | Cotrupe et al. . |
| 3,903,171 | 9/1975 | Toussaint et al. ............ 260/601 R |
| 4,273,945 | 6/1981 | Heilen et al. ............ 568/420 |
| 4,450,300 | 5/1984 | Fischer et al. ............ 568/462 |
| 4,451,677 | 5/1984 | Bradley et al. ............ 568/881 |

FOREIGN PATENT DOCUMENTS

| | | |
|---|---|---|
| 0 011 906 | 6/1980 | European Pat. Off. . |
| 0 541 871 | 5/1993 | European Pat. Off. . |
| 47-16434 | 9/1972 | Japan . |
| 51-24497 | 7/1976 | Japan . |
| 63-188642 | 8/1988 | Japan . |
| 781 405 | 8/1957 | United Kingdom . |
| 1 032 838 | 6/1966 | United Kingdom . |
| 87 07598 | 12/1987 | WIPO . |

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A process for the preparation of 3,3,5-trimethylcyclohexanone by catalytic hydrogenation of isophorone, wherein the hydrogenation is carried out in a plurality of two or more series-connected loops, wherein each loop involves the use of one reactor, which comprises:

(a) feeding isophorone and hydrogen to an upper part of a reactor to catalytically hydrogenate said isophorone to produce a hydrogenation product, (b) recycling a portion of said hydrogenation product back into said upper part of said reactor, (c) feeding the remainder of said hydrogenation product from said reactor to an upper part of a subsequent reactor wherein isophorone is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining 3,3,5-trimethylcyclohexanone from the product of step (e).

21 Claims, 1 Drawing Sheet

PROCESS FOR THE PREPARATION OF 3,3,5-TRIMETHYLCYCLOHEXANONE

BACKGROUND OF THE INVENTION

1. Field of the Invention

The present invention relates to a process for the preparation of 3,3,5-trimethylcyclohexanone (TMC-one) by catalytic hydrogenation of isophorone.

and the known processes are economically inefficient, the object of the present invention was to provide a process which enables high-grade TMC-one to be prepared in an economical manner.

In the hydrogenation of isophorone, essentially the following compounds are in thermodynamic equilibrium:

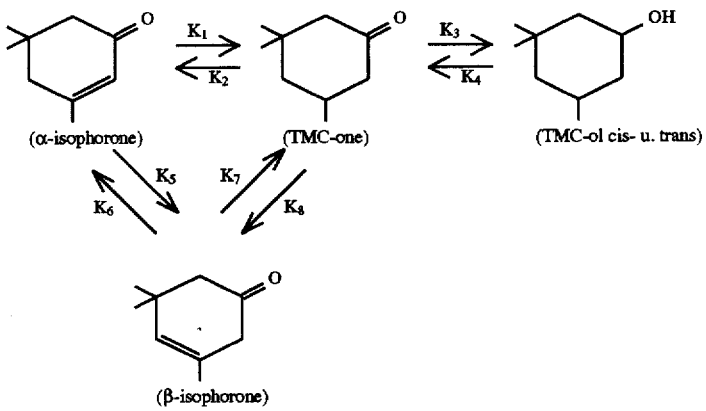

(α-isophorone)   (TMC-one)   (TMC-ol cis- u. trans)

(β-isophorone)

2. Discussion of the Background

TMC-one is used for the preparation of peroxides, as a precursor for perfumes, as a component of resins for coatings and as solvents.

Ketones can be prepared from unsaturated ketones by a) reduction with complex metal hydrides
b) transfer hydrogenation
c) hydrogenation with hydrogen.

Methods a) and b) have the disadvantage that coupling products arise and at least one work-up step is necessary.

It is known to hydrogenate isophorone selectively on pulverulent catalysts to form TMC-one. In JP 63 188 642 A, Raney nickel is disclosed as catalyst and isopropanol is used as solvent here. In Japanese Patent JP 47 016 434, Raney nickel is disclosed as catalyst and methanol as solvent. In the Patents JP 51 024 497 and JP 7 602 494, palladium catalysts having various support materials are claimed.

A disadvantage of the above processes is that they are carried out batchwise. After each batch, the catalyst must be separated off, which, in addition to the expense, leads to losses in handling. Reuse of the catalyst is only possible to a restricted extent. In addition, a distillation is necessary to recover the hydrogenation product when a solvent is used in the hydrogenation stage.

In US Def. Publ. 892 018, a process is described in which isophorone is passed together with hydrogen into a reaction column which contains, inter alia, a hydrogenation catalyst. A mixture of TMC-one and β-isophorone is separated off as overhead product. The β-isophorone in this mixture is isomerized at relatively high temperature. Pure TMC-one is then separated off as low-boiler. The remaining α-isophorone and the bottom product of the reaction column are recycled back into the process. This process has the disadvantage that it includes a total of four process steps.

Since many applications require a high quality TMC-one (TMC-one content>99%; isophorone content (α+β)<0.1%), The position of the equilibrium is a function, inter alia, of the temperature and the hydrogen pressure. Virtually pure TMC-one would only be obtainable under conditions under which the reaction $K_3$ virtually ceases.

SUMMARY OF THE INVENTION

It has now surprisingly been found that this object is achieved if the hydrogenation is carried out in a plurality of series-connected loops, preferably in a double loop procedure. In a suitable procedure, isophorone, together with hydrogenation discharge of the first reactor, is passed to the top of the first reactor. The amount of hydrogenation material from the first reactor equivalent to the fresh isophorone is fed, together with the hydrogenation discharge from the second reactor, to the top of the second reactor. More loops can also be connected downstream of the second. Hydrogenation material is removed from the product reservoir of the second or last reactor under level control.

DESCRIPTION OF THE PREFERRED EMBODIMENTS

Figure 1:
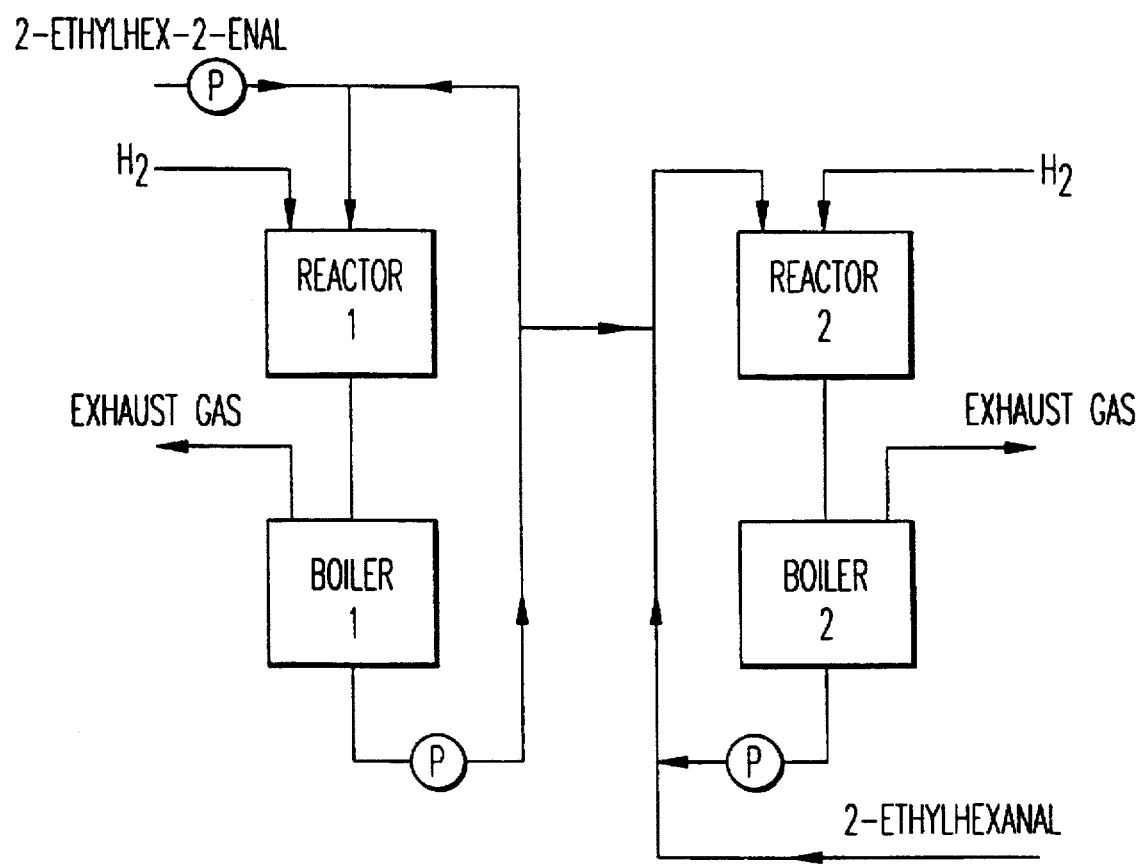
FIG. 1 is a block diagram illustrating the process of the invention.

The present process has the advantage that technical-grade isophorone (α+β-isophorone content≧99.7% by weight), which contains up to 1.6% by weight of β-isophorone, is hydrogenated to give a water-clear TMC-one (APHA<5) having a content >99% by weight, the residual isophorone content (Σα+β) being below 0.1% by weight. This corresponds to an isophorone conversion rate of greater than 99.9% and a selectivity greater than 99.3%.

It is particularly advantageous that, owing to the quality of the hydrogenation discharge, no work-up is necessary.

The present invention therefore relates to a process for the preparation of 3,3,5-trimethylcyclohexanone by catalytic hydrogenation of isophorone, wherein the hydrogenation is carried out in a plurality of two or more series-connected loops, wherein each loop involves the use of one reactor, which comprises:

(a) feeding isophorone and hydrogen to an upper part of a reactor to catalytically hydrogenate said isophorone to produce a hydrogenation product, (b) recycling a portion of said hydrogenation product back into said upper part of said reactor, (c) feeding the remainder of said hydrogenation product from said reactor to an upper part of a subsequent reactor wherein isophorone is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining 3,3,5-trimethylcyclohexanone from the product of step (e).

In the process of the invention, the hydrogenation is preferably carried out in two series-connected loops, isophorone, together with some of the hydrogenation product from the 1st reactor, being passed to the top of the 1st reactor, the remainder of the hydrogenation product from the 1st reactor, together with some of the hydrogenation product from the 2nd reactor, being passed to the top of the second reactor and 3,3,5-trimethylcyclohexanone being obtained from the remainder of the hydrogenation product from the 2nd reactor.

The hydrogenation can be carried out in the process of the invention in all reactors either in turbulent or in laminar flow. It can also be advantageous to carry out the hydrogenation in turbulent flow at least in the first reactor. Furthermore, here, hydrogenation is preferentially carried out in the liquid phase in all reactors.

Preferably, the hydrogenation in the process of the invention is carried out at temperatures of 30° to 200° C., particularly preferably at temperatures of 40° to 120° C. Furthermore, it can be advantageous to carry out the hydrogenation in the reactors at different temperature levels, for example, by operating the second or subsequent reactor at a lower temperature than the first or preceding reactor.

Generally, the process of the invention is operated under pressure. Preferably, the hydrogenation here is carried out in the reactors at pressures of 1 to 100 bar absolute, particularly preferably at pressures of 1 to 20 bar absolute. In addition, it can be advantageous to carry out the hydrogenation in the reactors at different pressure levels, for example by operating the second or subsequent reactor at a lower pressure than the first or preceding reactor.

In the process of the invention, the hydrogenation is preferably carried out in the reactors on a palladium catalyst, particularly preferably on a palladium catalyst applied to a support of aluminum oxide.

As the catalyst charge in the reactors, conventional hydrogenation catalysts suitable for this can be used, for example 0.5% Pd/Al$_2$O$_3$, (Engelhard).

The process of the invention enables particularly economic preparation of high-grade TMC-one in excellent yield and outstanding selectivity, so that the required product quality is achieved even without an additional product work-up.

Having generally described this invention, a further understanding can be obtained by reference to certain specific examples which are provided herein for purposes of illustration only and are not intended to be limiting unless otherwise specified.

EXAMPLES

Example 1

The hydrogenation apparatus, as shown in FIG. 1, has two reactors of the same type having the following dimensions: $\phi_c$=42 mm; l=1,500 mm.

Both reactors are each packed with 1.9 l of ENGELHARD catalyst 0.5% Pd/Al$_2$O$_3$.

Technical-grade isophorone ($\Sigma\alpha+\beta$99.7% by weight), diluted with partially hydrogenated isophorone (from boiler 1), is passed to the top of the first reactor (first loop).

The amount of hydrogenation material equivalent to the isophorone used is passed from boiler 1 under level control to the loops of the second reactor. TMC-one is removed under level control from the boiler 2.

The following reaction conditions are present in the reactors:

|  | Reactor 1 | Reactor 2 |
| --- | --- | --- |
| Throughput | 1.45 kg/h | approx. 1.46 kg/h |
| Circulation | 100 kg/h | 80 kg/h |
| H$_2$ pressure | 15 bar | 10 bar |
| Mean temperature | 100° C. | 40° C. |
| Exhaust gas rate | 120 l(S.T.P.)/h | 1 l(S.T.P.)/h |

After the quasi steady-state has been established, the hydrogenation material obtained has a TMC-one content of 99.1% by weight. The residual content of isophorone ($\Sigma\alpha+\beta$) is 0.05% by weight.

Comparison Example

In contrast to Example 1, the circulation of the second reactor (circulation rate 0) is switched off. All other reaction conditions are identical to those in Example 1.

A hydrogenation material is obtained having a TMC-one content of only 97.6% by weight. The residual isophorone content ($\Sigma\alpha+\beta$) is $\leq$0.05% by weight.

The disclosure of German patent application 195 24 969.0, filed Jul. 8, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for the preparation of 3,3,5-trimethylcyclohexanone by catalytic hydrogenation of isophorone, wherein the hydrogenation is carried out in a plurality of two or more series-connected loops, wherein each loop involves the use of one reactor, which comprises:

(a) feeding isophorone and hydrogen to an upper part of a reactor to catalytically hydrogenate said isophorone to produce a hydrogenation product, (b) recycling a portion of said hydrogenation product back into said upper part of said reactor, (c) feeding the remainder of said hydrogenation product from said reactor to an upper part of a subsequent reactor wherein isophorone is catalytically hydrogenated to produce a subsequent hydrogenation product, and wherein a portion of said subsequent hydrogenation product has been recycled and is fed with said remainder of said hydrogenation product to said upper part of said subsequent reactor, (d) repeating step (c) until the subsequent reactor is the last reactor, (e) recovering the remainder of said subsequent hydrogenation product from said last reactor, and (f) obtaining 3,3,5-trimethylcyclohexanone from the product of step (e).

2. A process as claimed in claim 1, wherein the hydrogenation is carried out in two series-connected loops.

3. A process as claimed in claim 1, wherein hydrogenation is carried out in the liquid phase in all reactors.

4. A process as claimed in claim 2, wherein hydrogenation is carried out in the liquid phase in all reactors.

5. A process as claimed in claim 1, wherein the flow is laminar in all reactors.

6. A process as claimed in claim 2, wherein the flow is laminar in all reactors.

7. A process as claimed in claim 3, wherein the flow is laminar in all reactors.

8. A process as claimed in claim 1, wherein the flow is turbulent in all reactors.

9. A process as claimed in claim 2, wherein the flow is turbulent in all reactors.

10. A process as claimed in claim 3, wherein the flow is turbulent in all reactors.

11. The process as claimed in claim 1, wherein the hydrogenation is carried out at temperatures of 30° to 200° C.

12. The process as claimed in claim 2, wherein the hydrogenation is carried out at temperatures of 30° to 200° C.

13. The process as claimed in claim 11, wherein the hydrogenation is carried out at temperatures of 40° to 120° C.

14. The process as claimed in claim 12, wherein the hydrogenation is carried out at temperatures of 40° to 120° C.

15. The process as claimed in claim 1, wherein the hydrogenation is carried out in the reactors operating at different temperature levels.

16. The process as claimed in claim 1, wherein the hydrogenation is carried out at pressures of 1 to 100 bar absolute.

17. The process as claimed in claim 16, wherein the hydrogenation is carried out at pressures of 1 to 20 bar absolute.

18. The process as claimed in claim 1, wherein the hydrogenation is carried out in the reactors operating at different pressure levels.

19. The process as claimed in claim 1, wherein the hydrogenation is carried out on a palladium catalyst.

20. The process as claimed in claim 19, wherein the hydrogenation is carried out on a palladium catalyst which is applied to a support of aluminum oxide.

21. The process as claimed in claim 1, wherein the hydrogenation is carried out on a pulverulent hydrogenation catalyst for the formation of 3,3,5-trimethylcyclohexanone.

* * * * *

UNITED STATES PATENT AND TRADEMARK OFFICE
CERTIFICATE OF CORRECTION

PATENT NO. : 5,728,891
DATED : March 17, 1998
INVENTOR(S) : Wilfried BUESCHKEN, et al.

It is certified that error appears in the above-identified patent and that said Letters Patent is hereby corrected as shown below:

On the title page, item [30] should be:

--[30]     Foreign Application Priority Data
     Jul. 8, 1995   [DE]  Germany  .........  195 24 969.0--

Signed and Sealed this

Twelfth Day of May, 1998

Attest:

BRUCE LEHMAN

*Attesting Officer*     Commissioner of Patents and Trademarks